(12) United States Patent
Hara (10) Patent No.: US 9,622,653 B2
(45) Date of Patent: Apr. 18, 2017

(54) PERIMETER

(71) Applicant: Kowa Company, Ltd., Nagoya-shi, Aichi (JP)

(72) Inventor: Takuya Hara, Hamamatsu (JP)

(73) Assignee: Kowa Company, Ltd, Aichi (JP)

( * ) Notice: Subject to any disclaimer, the term of this patent is extended or adjusted under 35 U.S.C. 154(b) by 0 days.

(21) Appl. No.: 14/420,511

(22) PCT Filed: Jul. 26, 2013

(86) PCT No.: PCT/JP2013/070279
§ 371 (c)(1),
(2) Date: Feb. 9, 2015

(87) PCT Pub. No.: WO2014/024700
PCT Pub. Date: Feb. 13, 2014

(65) Prior Publication Data
US 2015/0201828 A1    Jul. 23, 2015

(30) Foreign Application Priority Data

Aug. 10, 2012 (JP) ................................. 2012-177967

(51) Int. Cl.
*A61B 3/14* (2006.01)
*A61B 3/00* (2006.01)
(Continued)

(52) U.S. Cl.
CPC .......... *A61B 3/0025* (2013.01); *A61B 3/0058* (2013.01); *A61B 3/024* (2013.01); *A61B 3/14* (2013.01); *A61B 3/1225* (2013.01)

(58) Field of Classification Search
CPC .................................. A61B 3/024; A61B 3/14
(Continued)

(56) References Cited

U.S. PATENT DOCUMENTS

| 6,247,812 | B1 * | 6/2001 | Miehle | ..................... A61B 3/10 |
| | | | | 351/206 |
| 2007/0222946 | A1 * | 9/2007 | Fukuma | ................. A61B 3/102 |
| | | | | 351/206 |

(Continued)

FOREIGN PATENT DOCUMENTS

| JP | 10-309264 A | 11/1998 |
| JP | 246991 A | 9/2006 |

(Continued)

OTHER PUBLICATIONS

International Search Report dated Aug. 20, 2013.

*Primary Examiner* — Mahidere Sahle
(74) *Attorney, Agent, or Firm* — Law Offices of Robert F. Zielinski LLC (57) ABSTRACT

A perimeter 2 for measuring a visual field by conducting perimetry operations regarding measurement points RG of the subject eye 22a has means 17 for storing perimetry result, means 10, 24 for composing the perimetry result as a map image corresponding to a fundus and indicating it on the display 20, means 13 for obtaining and indicating a structure examination image PC1 of the subject eye 22a, means 16 for superimposing the map image MAP2 on the indicated structure examination image PC1 and indicating the superimposed as a composite image PC2, and means 15 for setting a concerned area NA on the composite image PC2, and means 21 for computing an evaluation value of the perimetry based upon the perimetry result.

4 Claims, 8 Drawing Sheets

(51) Int. Cl.
*A61B 3/024* (2006.01)
*A61B 3/12* (2006.01)

(58) Field of Classification Search
USPC ................................................ 351/200–247
See application file for complete search history.

(56) References Cited

U.S. PATENT DOCUMENTS

| 2011/0234980 | A1* | 9/2011 | Hara | ...................... | A61B 3/024 |
| | | | | | 351/224 |
| 2011/0292342 | A1* | 12/2011 | Maddess | .................. | A61B 5/40 |
| | | | | | 351/209 |

FOREIGN PATENT DOCUMENTS

| JP | 319408 A | 12/2007 |
| JP | 206144 A | 10/2011 |
| JP | 510830 A | 5/2012 |

\* cited by examiner

PERIMETER

TECHNICAL FIELD

The invention relates to a perimeter that is possible to compute, indicate and confirm a change of examination result of the perimeter over time with only portion showing a structural abnormality.

BACKGROUND ART

In a perimetry (threshold value examination), it is possible to obtain sensitivity for light stimulation in each retina part, and it is possible to judge a progress of a disease in glaucoma by confirming the change of such a sensitivity over time.

In many perimetry, a difference between the normal value in each examination point and the examination result is computed and the means value of the computed values is used as an index (MD slope and the like). Such a mean value may be a simple mean value of the whole visual field, or may be weighting mean value by preparing the weighting factor in each portion of the visual field (in a conventional perimeter, the dispersion of the normal eye data in each portion is determined as the weighting factor).

The reason for adopting such a weighting factor is that the center of the visual field is more important than the peripheral portion thereof and its importance is different even in the same depression of 1 dB. The weighting factor may be computed from the standard deviation of the normal data as the conventional perimeter, or a ratio to the decibel value till the percentile designated from the normal value. The same result is obtained in the former and the latter if the data shows a normal distribution, but the latter is considered to be useful in the distribution where the area is wide on the side of the lower values as the peripheral portion of the visual field since the actual distribution can be reflected.

Furthermore, at the initial stage of the glaucoma, the sensitivity depression is seen in a part of the retina not but the whole thereof, and the area broadens with the progress of the disease. For this reason, there is a perimeter for indicating the change with time in each examination point. A function of such a product is to indicate the change with time in each portion of the visual field and to search whether statistically significant depression can be seen in each regression. There is such a report that the progress can be grasped by the MD (mean deviation), in which only portion showing significant depression is extracted, faster than the change with time of the whole MD value.

However, the following problems remain at the present.
(1) In the judgment of the progress, one that obtains the statistically significant inclination is extracted, but it is not always the portion showing the glaucoma-related structural abnormality.
(2) Severity of the depression in each point is not considered (all depressions are evaluated with the same standard).

Then, the proposed system is that a concerned area is designated from the perimetry result and the change with time for the concerned area is computed and measured (patent related document 1).

PRIOR ART

Patent Related Document

[Patent related document 1]: Japanese Patent Application Publication No. H10-309264

DISCLOSURE OF INVENTION

Problems to be Solved by Invention

In the method of designating the concerned area from the perimetry result so as to predict the abnormal area, such a state that the condition is already progressed is watched. For this reason, there is a risk that taking the countermeasures is delayed. In recent information, the structural abnormality appears earlier than the visual field, so in a desired configuration, the structural abnormality of the eye is detected with the device for detecting structural abnormality, such as a fundus camera, an OCT (optical coherence tomography) and a SLO (scanning laser ophthalmoscopy), and the future abnormality of the visual field in the glaucoma and the like can be predicted.

An object of the invention is to provide the perimeter for detecting the structural abnormality of the eye, and computing, indicating and confirming the examination result of the perimeter with only the portion showing the structural abnormality, and for predicting the future occurrence of the abnormality of the visual field.

Means for Solving Problems

A first aspect of the invention is a perimeter (2) for measuring a visual field of a subject eye (22a) by conducting predetermined perimetry operations for two or more measurement points (RG) of the subject eye (22a) comprising:
  a memory (17) that stores perimetry results;
  a perimetry result indicator (10, 24) that composes the perimetry result as a map image (MAP1, MAP2) that corresponds to a fundus and indicates it on a display (20);
  an structure examination image indicator (13) that obtains a structure examination image (PC1) of the subject eye (22a) on which the perimetry is conducted and indicates the obtained image on the display (20);
  a composite image preparing means (16) that superimposes the map image (MAP2) on the displayed structure examination image (PC1) and indicates the superimposed on the display (20) as a composite image (PC2);
  a concerned area setter (15, 19) that sets a concerned area (NA) on the composite image (PC2); and
  an evaluation value computer (21) that computes an evaluation value (MD value and the like) of the perimetry regarding the concerned area (NA) based upon the perimetry result and outputs it.

The second aspect of the invention is the perimeter (2), wherein the map image (MAP1, MAP2) is comprised of two or more divided area (RG) that correspond to the measurement points, and the concerned area setter (15, 19) sets the concerned area (NA) from two or more divided areas (RG).

The third aspect of the invention is the perimeter (2), wherein a weighting factor is set on each divided area (RG), and the evaluation value computer (21) computes the evaluation value of the perimetry (with equation (1)) as mean value (the weighting is the inverse value of the square of the standard deviation) of the divided areas (RG) that comprises the concerned areas with the weighting factor.

The fourth aspect of the invention is the perimeter (2), wherein the evaluation value computer (21) also computes the evaluation value of the whole visual field of the subject eye based upon the perimetry result and outputs it together with the evaluation value of the concerned area.

The fifth aspect of the invention is the perimeter (2), wherein the memory (17) stores the perimeter results of the subject eye (22a) in different times, and the evaluation value computer (21) respectively computes and outputs the evaluation values of the perimetry at two or more points of time that are respectively different.

The sixth aspect of the invention is the perimeter (2), wherein the concerned area setter (15, 19) is able to set two or more concerned areas, and the evaluation value computer (21) computes and outputs the evaluation values for the respective concerned areas.

The seventh aspect of the invention is the perimeter (2), wherein the memory (17) stores a normal threshold value (such as, the mean threshold value of a normal person) of each measurement point of the perimetry, and the perimeter further comprising:
  a threshold value measuring means (10) that measures a lowest value of brightness of a stimulus to which the subject eye can respond for two or more measurement points so as to obtain a threshold value examination result in each measurement point;
  wherein the perimetry result indicator (10) computes a deviation value regarding each measurement point (RG) from the measured threshold value examination result based upon the normal threshold value stored in the memory (17), and has a map image composer (24) that composes the map image (MAP2) showing a total deviation result which is comprised of these deviation values.

The eighth aspect of the invention is the perimeter (2), further comprising a structural abnormality designator that sets a structural abnormality portion (UP) on the structure examination image (PC1) indicated on the display, and indicate the set structural abnormality portion (UP) on the structure examination image (PC1).

The ninth aspect of the invention is a perimetric method for measuring a visual field of a subject eye (22a) by conducting predetermined perimetric operations for two or more measurement points (RG) of the subject eye (22a), comprising the following steps:
  a step of storing perimetry results in a memory (17);
  a step of composing the perimetry result as a map image (MAP1, MAP2) that corresponds to a fundus and indicates it on the display (20);
  a step of obtaining a structure examination image (PC1) of the subject eye (22a) on which the perimetry is conducted and indicates the obtained image on the display (20);
  a step of superimposing the map image (MAP2) on the indicated structure examination image (PC1) and indicating the superimposed on the display (20) as the composite image (PC2);
  a step of setting a concerned area (NA) on the composite image (PC2); and
  a step of computing an evaluation value (MD value) of the perimetry regarding the concerned area (NA) based upon the perimetry result.

The tenth aspect of the invention is the perimetric method, further comprising a step of setting a structural abnormality portion (UP) on the structure examination image (PC1) indicated on the display (20) and of displaying the set structural abnormality portion (UP) on the structure examination image (PC1).

Effects of Invention

According to the first through ninth aspects of the invention, the concerned area is set on the composite image obtained by superimposing the map image on the structure examination image and the evaluation value of the perimetry is computed in the concerned area. So, it is possible to detect the structural abnormality of the eye with the structure examination image, such as the fundus image, and at the same time, it is possible to compute, indicate and confirm the state of the visual field of the subject eye with only the portion showing the structural abnormality by utilizing the examination result of the perimeter, and to provide the perimeter and the method of measuring the visual field through which the future occurrence of the abnormality of the visual field can be predicted.

According to the second aspect of the invention, it is possible to properly correspond the structure examination image and the measurement result of the perimetry to each other since the divided area that designates the concerned area corresponds to the measurement point of the perimetry.

According to the third aspect of the invention, it is possible to obtain the evaluation value under consideration of the significance according to the position in the visual field where the respective divided areas exist by setting the weighting factor on each divided areas.

According to the fourth aspect of the invention, it is possible to compare the concerned area and the evaluation value of the whole visual field with each other and to properly judge the progress of the disease.

According to the fifth aspect of the invention, it is possible to obtain the evaluation value of the perimetry at two or more points of time that are respectively different, and to easily confirm the change of the visual field over time.

According to the sixth aspect of the invention, it is possible to take countermeasures by setting two or more concerned areas even if two or more structural abnormality portions are found or the shape of the structural abnormality portion is complex.

According to the seventh aspect of the invention, it is possible to easily recognize a condition separated from the standard condition on the image since the total deviation result comprised of the deviation to the normal threshold value of each measurement point is indicated on the map image.

According to the eighth through tenth aspects of the invention, it is possible to compare the structural abnormality portion and the perimetry result with each other by indicating the structural abnormality portion on the structure examination image.

The number in parentheses shows the corresponding element in the drawings for the sake of convenience, accordingly, the descriptions are not restricted and bound by the descriptions on the drawings.

BRIEF DESCRIPTION OF DRAWINGS

FIG. 8 is a view that shows computed change with time of the concerned area, (a) is a table of the change with time and (b) is a graph of the change with time.

PREFERRED EMBODIMENT

An embodiment of the invention is now explained, referring to appended drawings.

Figure 1:
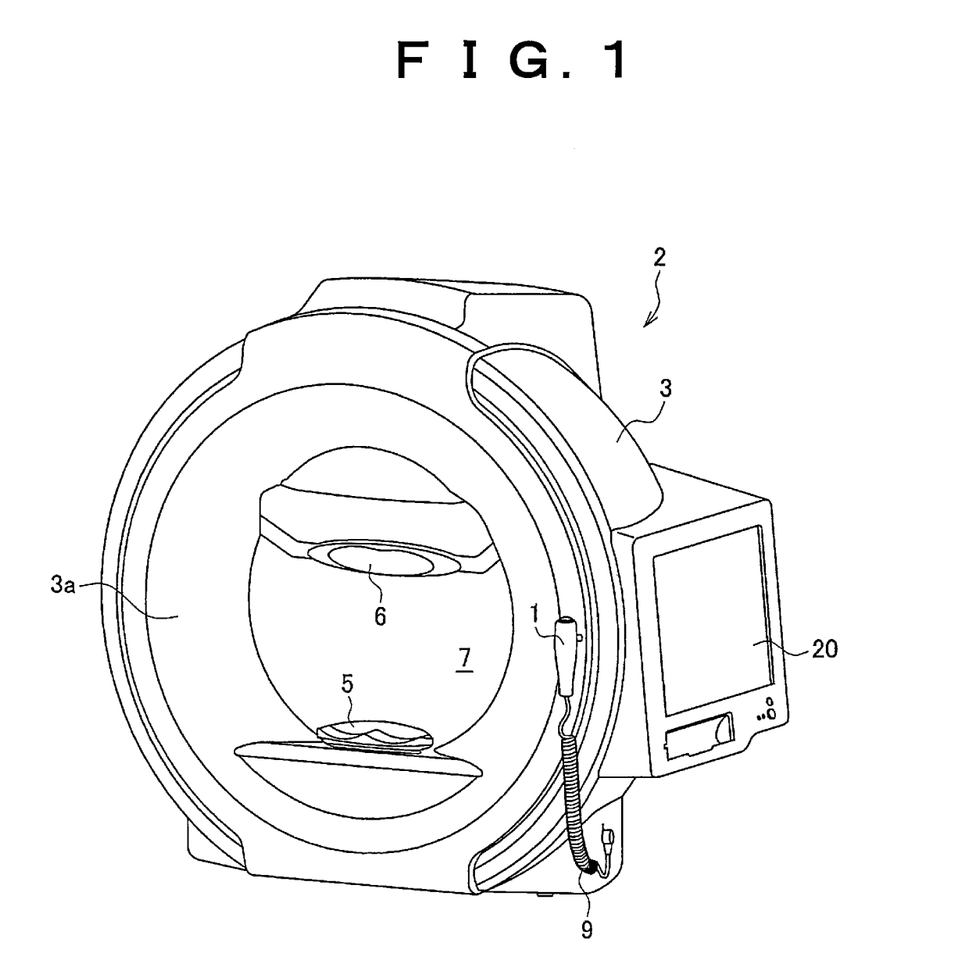
FIG. 1 is a perspective view that shows an example of a perimeter to which the invention is applied.

As shown in FIG. 1, a perimeter 2 has a main body 3 the whole of which is in the shape of a box, and a jaw stand 5 and a forehead pad 6 are provided at a front face 3a of the main body 3. A response switch 1 is attachably and detachably located on a right side of FIG. 1 of the main body 3 through a connection flex 9, and a visual field dome 7 in a semi-spherical shape through which stimuli are presented, is provided at a front hand of the jaw stand 5 and the forehead pad 6, that is, inside the main body 3 on a back side of a paper of FIG. 1. The visual field dome 7 is configured so as to project stimulus for perimetry (not shown) at optional positions in the visual field dome 7 through a visual field measurer 10 that is built in the main body 3.

Figure 2:
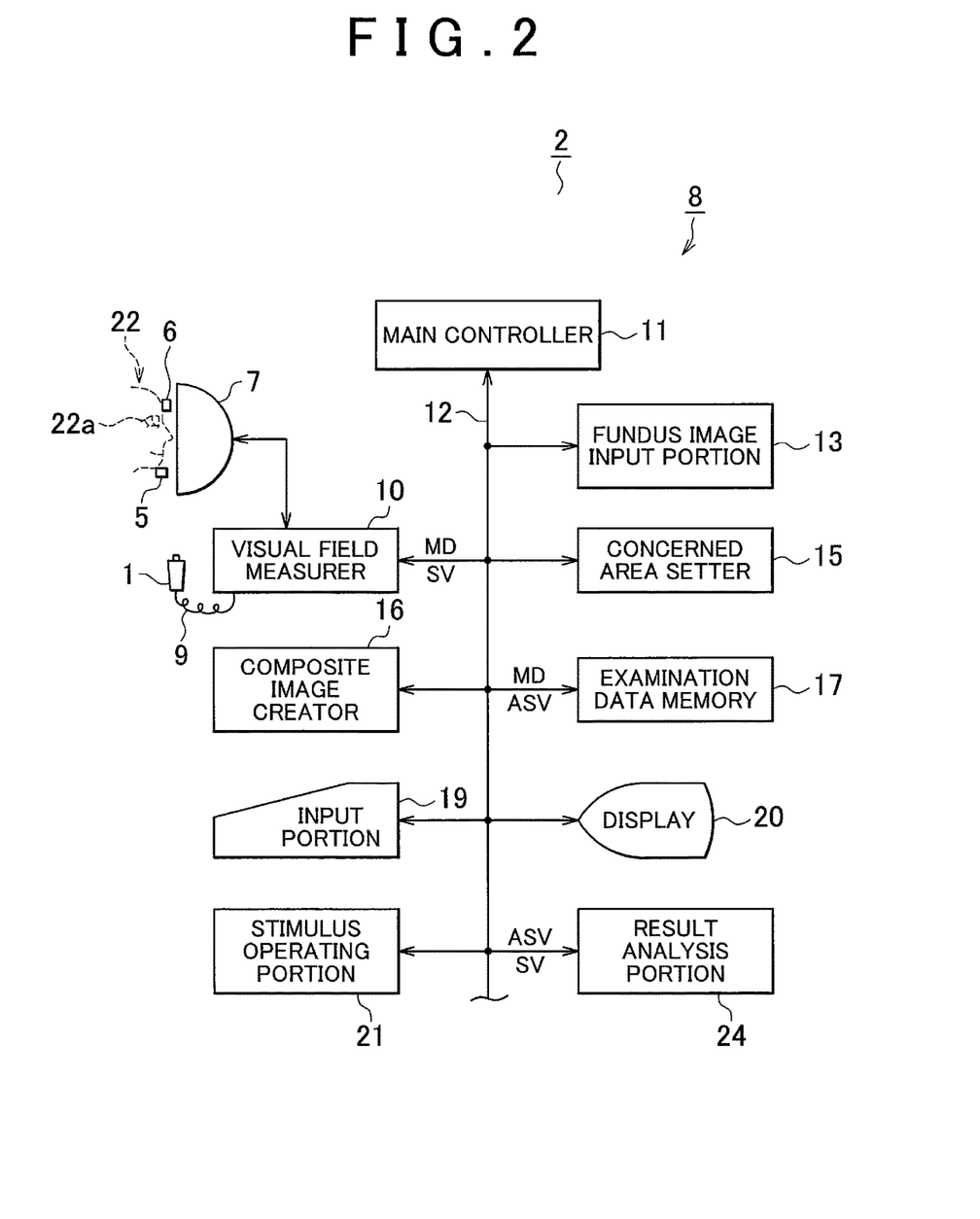
FIG. 2 is a control block diagram that shows an example of control portions of the perimeter of FIG. 1.

Besides, as shown in FIG. 2, a controller 8 of the perimeter 2 is provided inside the main body 3, and the controller 8 has a main controller 11. A fundus image input portion 13, the above-mentioned visual field measurer 10, a concerned area setter 15, a composite image creator 16, an examination data memory 17, an input portion 19, such as a keyboard, a display 20, a stimulus operating portion 21, a result analysis portion 24 are connected with the main controller 11 via a bus line 12. A control block diagram as shown in FIG. 2 shows only portions that relate to the invention and does not show the other constitutional portions of the perimeter 2 that are not relate to the invention.

The perimeter 2 has the above-mentioned structure. In order to measure a visual field of subject eyes 22a of an examinee 22 so as to use for diagnoses for a glaucoma and the like, an examinee is invited to put his (her) jaw on the jaw stand 5 and contact his (her) forehead with the forehead pad 6 so as to be pressed against such a pad such that the subject eye 22a of the examinee 22 is located at a predetermined perimetry position, as shown in FIG. 2.

When an operator instructs the perimeter 2 a start of a visual field measurement operation through the input portion 19 in the afore-mentioned state, the main controller 11 instructs the visual field measurer 10 to measure the visual field of the subject eye 22a. Receiving such an instruction, the visual field measurer 10 presents the stimuli (not shown) in order at proper positions inside the visual field dome 7 with a well-known method of visual field measurement. At the results, as shown in FIG. 5(a), minimum values of brightness of the stimuli to which the examinee can respond regarding two or more measurement points on a measurement coordinate system CS (that are indicated with many square areas RG in the figure and correspond to respective portions of a retina) are measured and collected, and these values, threshold values SV, are indicated on the display 20 with numeral numbers as a map image MAP1. Such a map image MAP1 is comprised of two or more areas RG that correspond to the above-mentioned measurement points. An origin ZP of the measurement coordinate system CS in the figure that is used for the visual field measurement (perimetry) is set, corresponding to a center position of a macula lutea of the subject eye 22a, and blanks in the figure are the measurement points to which the examinee does not respond or on which the measurement is not conducted. In case of FIG. 5(a), the measurement points that correspond to two areas RGb and RGb are ones that correspond to blind spots.

When the examinee perceives the stimulus presented on the visual field dome 17 through the subject eye 22a at the time of the measurement, he (or she) operates the response switch 1. If not perceived, the examinee does not operate the response switch 1. So, it is possible for the visual field measurer 10 to obtain the measurement results regarding the respective measurement points, as shown in FIG. 5(a), relating the state of the operation of the response switch 1 and the position and the brightness of the stimulus inside the visual field dome 7 at this time to each other. In the measurement results of FIG. 5(a), the value of the threshold value SV is a reaction threshold value of the subject eye 22a and is referred to as threshold value examination result SHR for this reason.

Figure 5:
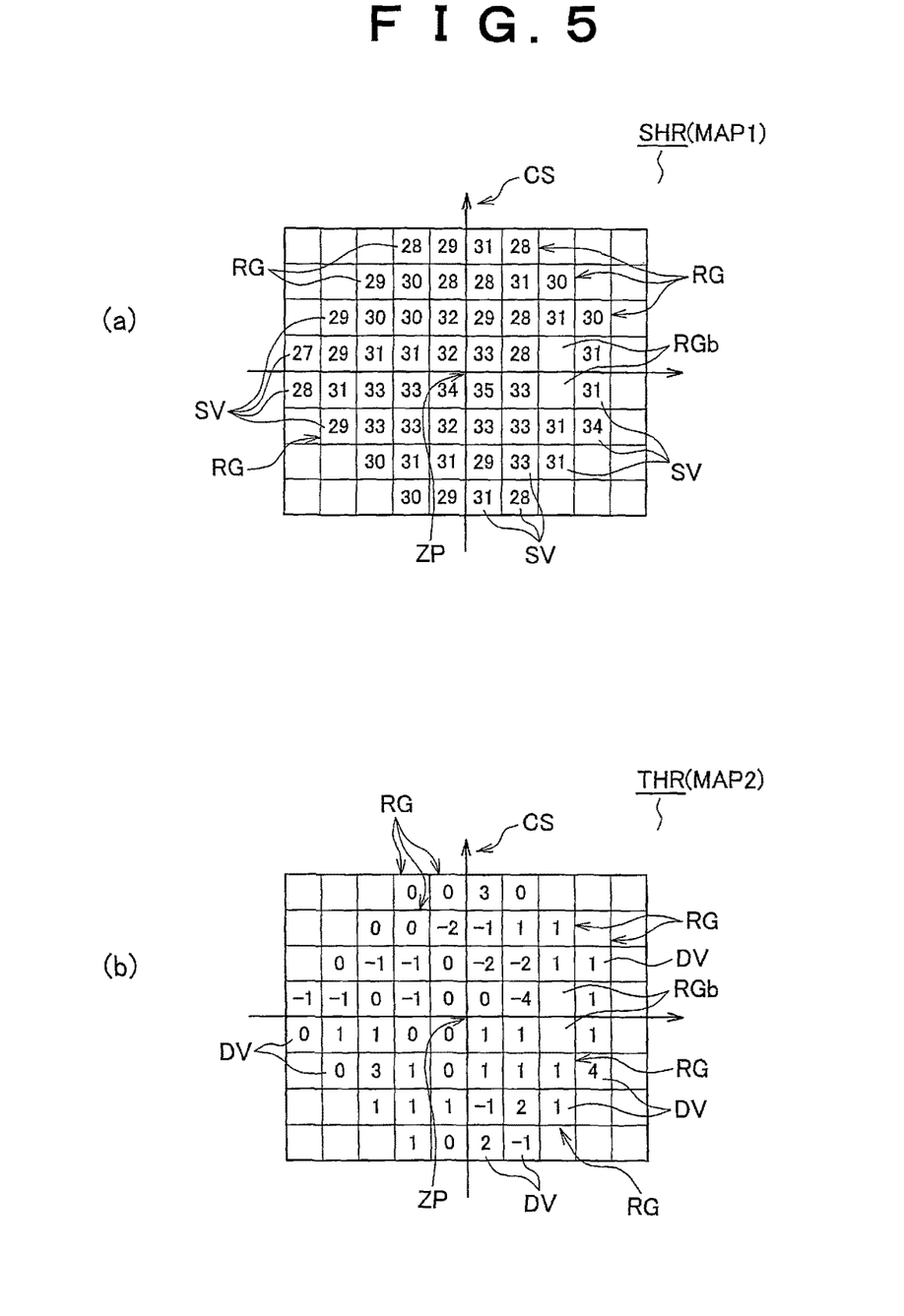
FIG. 5 shows an example of perimetry measurement data of an subject eye of the fundus photograph of FIG. 3, (a) is a view that shows a map image showing an example of a threshold value examination result of the perimetry, and (b) is a view that shows a map image of a total deviation to the examination result of (a).

After thus obtaining the threshold value examination result SHR regarding the subject eye 22a, the main controller 11 instructs the result analysis portion 24 to compute a total deviation regarding each measurement point of the obtained threshold value examination result SHR and to display a total deviation result THR. Receiving such an instruction, the result analysis portion 24 reads a normal threshold value ASV regarding each measurement point of the visual field measurement out of the examination data memory 17 and computes a difference between both as a deviation value DV and prepare a map image MAP2 on which the deviation value DV regarding each measurement point is indicated, corresponding to a fundus visual field area and indicates this image on the display 20, as shown in FIG. 5 (b). In such a case, the normal threshold value ASV may be a mean value of the measurement results of many subject eyes, or may be a proper value, such as a median of the measurement results of the subject eyes since it is the threshold value that is regarded as the normal value in each measurement point. In the map image MAP2 of the total deviation result THR of FIG. 5(b), the area RG on which "0 (zero)" is indicated as the deviation value DV is the measurement point in which the measurement threshold value SV and the normal threshold value ASV are equal to each other, and the area RG on which a positive number, such as "1" and "2" is indicated is the measurement point in which the measured threshold value SV is higher than the normal threshold value ASV in the sensitivity, and the area RG on which a negative number, such as "−1" and "−2" is indicated is the measurement point in which the measured threshold value SV is lower than the normal threshold value ASV in the sensitivity. The obtained threshold value examination result SHR, the total deviation results THR, and their map images MAP1 and MAP2 are respectively stored in an area in the examination data memory 17, attaching ID data corresponding to the subject eye 22a thereto as measurement data of the subject eye 22a of the examinee 22.

Figure 3:
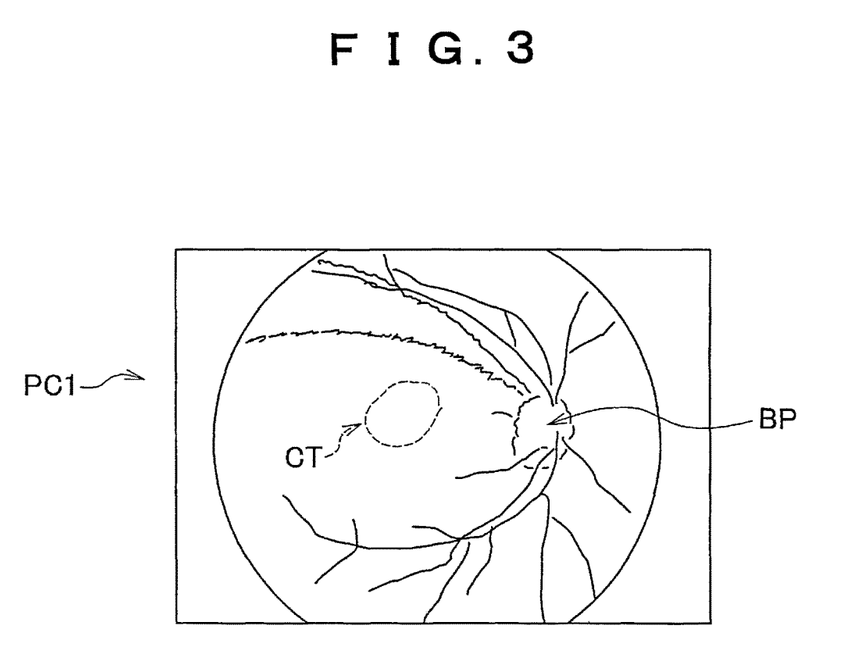
FIG. 3 is a typical view that shows an example of a fundus photograph that is a structure examination image.

After thus finishing the perimetry on the subject eye 22a, the operator instructs to indicate a structure examination image of the subject eye 22a on which examination is finished on the display 20 through the input portion 19. Receiving such an instruction, the main controller 11 instructs the fundus image input portion 13 to obtain the structure examination image PC1 of the subject eye 22a on which the examination is finished and to indicate it on the display 20. The fundus image input portion 13 reads the structure examination image PC1 of the subject eye 22a that is already stored in the examination data memory 17, such as a fundus image, that is obtained through a structural abnormality detecting apparatus, such as a fundus camera, an OCT (optical coherence tomography) and a SLO (scanning laser ophthalmoscope), and indicates it on the display 20, as shown in FIG. 3. In such a case, it is not always necessary for the fundus image input portion 13 to obtain the data that is stored in the examination data memory 17 as the structure examination image PC1, and it may be sufficient to obtain the structure examination image PC1 regarding the subject eye 22a that is stored in the structural abnormality detecting apparatus on-line connecting with the perimeter 2 through a communication line (it may be the structure examination image PC1 that is obtained through the structural abnormality detecting apparatus after or before the perimetry). Otherwise, the structure examination image data that is stored in a proper portable memory element may be read.

Figure 4:
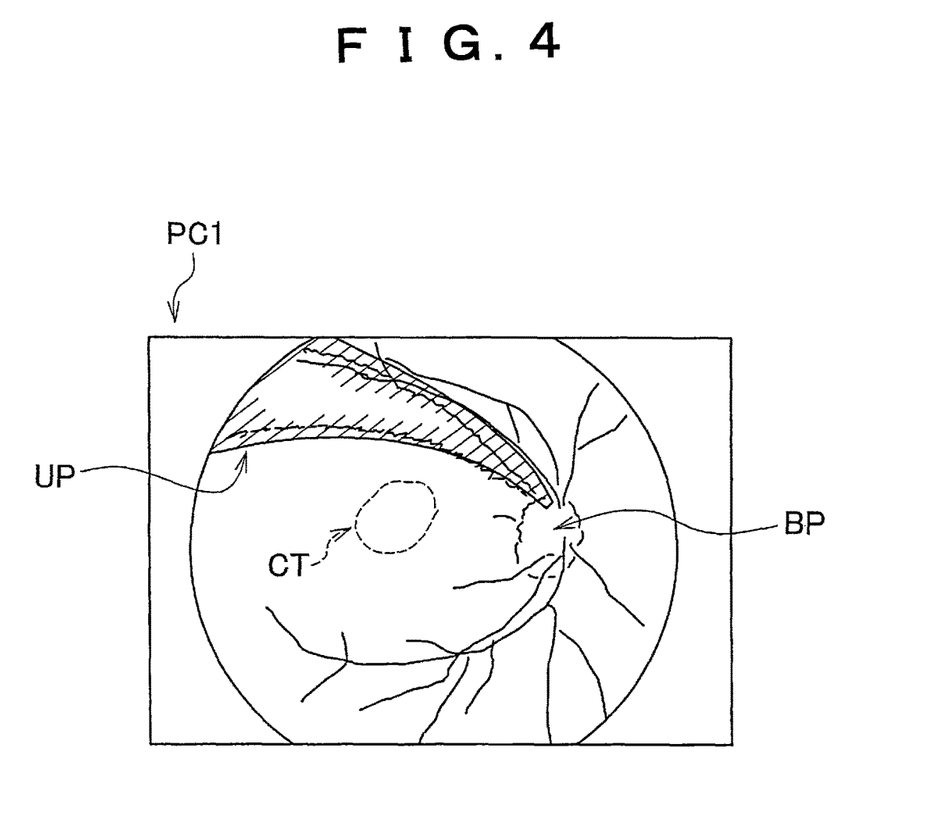
FIG. 4 is a view of the fundus photograph of FIG. 3 on which an abnormality portion is marked.

After indicating the structure examination image PC1 on the display 20 as shown in FIG. 3, the operator (a doctor) judges a portion having a structure abnormality, referring to the structure examination image PC1, and chooses and designates the portion on the display 20 as a structural abnormality portion UP through the input portion 19. Then, the composite image creator 16 marks the portion designated on the structure examination image PC1 of the display 20 as the structural abnormality portion UP, and is indicated as shown in FIG. 4. A portion that spreads out into a laterally slim triangle form from a blind point portion BP for the left in FIG. 4 is the marked structural abnormality portion UP. Such a structural abnormality portion UP may be extracted by the operator, but can be automatically extracted by image judgment by judging variation of the brightness that appears on the structural abnormality portion UP of the structure examination image PC1 to the surrounding.

Subsequently, the operator instructs the main controller 11 through the input portion 19 to indicate the structure examination image PC1 indicated on the display 20, that is obtained by superimposing the total deviation result THR of the perimetry result for the subject eye 22a on which perimetry finishes thereon. In this case, such a procedure may be automatically done through the main controller 11 without waiting an instruction from the operator according to a processing program stored in a memory (not shown) at a stage when the structure examination image PC1 is obtained or a stage when the operator extracts the structural abnormality portion UP.

Figure 6:
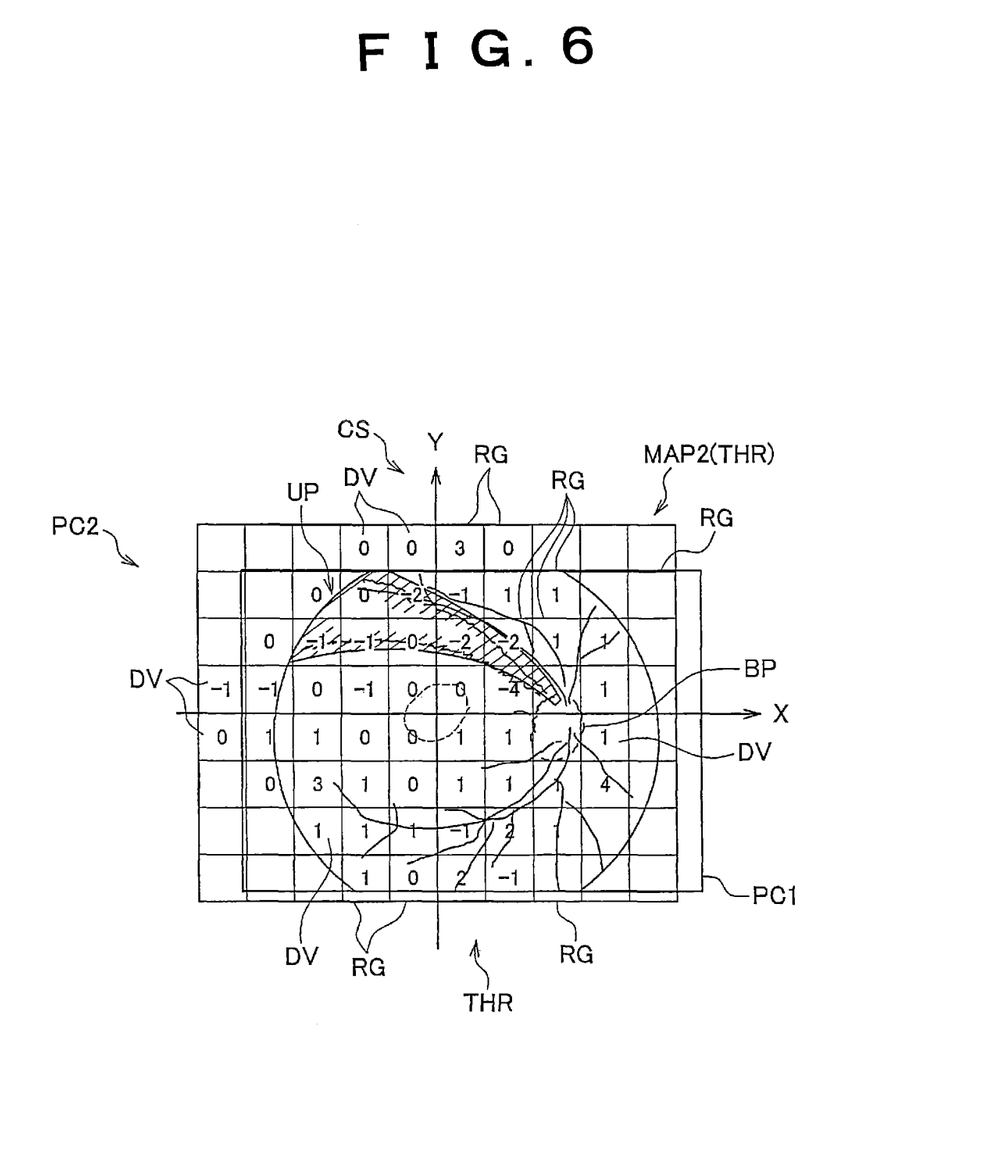
FIG. 6 is a typical view obtained by superimposing the total deviation of FIG. 5(b) on the fundus photograph of FIG. 4.

The main controller 11 which received the instruction of indicating of the structure examination image PC1 obtained by superimposing the total deviation result THR of the perimetry result for the subject eye 22a on which perimetry finishes thereon instructs the composite image creator 16 to indicate the composite image PC2 as shown in FIG. 6 on the display 20 as the composite image PC2, which superimposes the map image MAP2 of the total deviation result THR as shown in FIG. 5(b) on the structure examination image PC1 from which the structural abnormality portion UP of FIG. 4 was extracted. It is possible to easily do such a procedure by superimposing the center of macula lutea CT of the structure examination image PC1 on the origin ZP of the map image MAP2 of the total deviation result THR and superimposing the blind point BP of the structure examination image PC1 on the areas RGb, RGb of the map image MAP2 of the total deviation result THR so as to respectively watch the both since the origin ZP of rectangular coordinates CS of the map image MAP2 of the total deviation result THR of FIG. 5(b) corresponds to the center of the macula lutea (CT of FIG. 4) of the subject eye 22a and the measurement points corresponding to the areas RGb, RGb correspond to the blind point BP.

Then, the display 20 indicates the composite image PC2 which superimposes the map image MAP2 of the total deviation result THR on the structure examination image PC1 as shown in FIG. 6, and it is possible to watch the subject eye 22a, visually comparing the abnormality portion UP and the total deviation result THR with each other since the abnormality portion UP is extracted in advance and indicated on the structure examination image PC1. As clear from FIG. 6, the structure abnormality portion UP that was extracted on the structure examination image PC1 almost corresponds to the area RG on which negative numbers, such as "−1" and "−2" are indicated as the total deviation result THR, that is, the abnormality portion in which the measured threshold value SV is lower than the normal threshold value ASV in their sensitivities. However, the other abnormality portion in which the measured threshold value SV is lower than the normal threshold value ASV in their sensitivities can be seen in addition to the structure abnormality portion UP. On the other hand, there is the structure abnormality portion UP in which the abnormality of the visual field (the portion which deviation value DV is zero) does not appear in the perimetry. Generally, it is said the structural abnormality of an eye fundus is detected earlier than a functional abnormality of the perimetry, and it is common the examination result of the perimetry is normal even in the periphery of the structure abnormal portion of the eye fundus. However, when disease is progressing, it is thought the abnormality of the visual field is detected at the periphery of the structural abnormality portion with higher possibilities.

Figure 7:
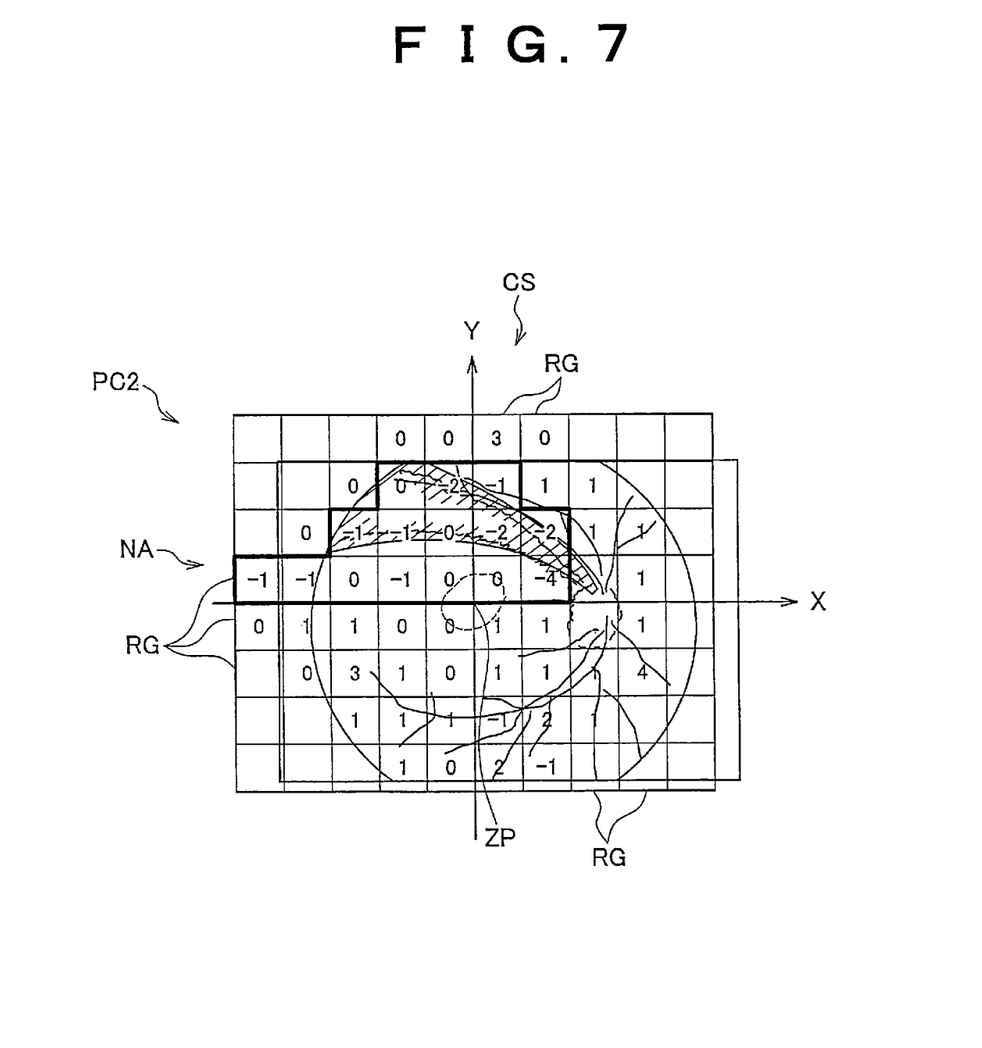
FIG. 7 is a typical view that shows a state that a concerned area is selected on the superimposed indication of FIG. 6.

The operator (the doctor) designates concerned areas NA to be monitored regarding change-with-time by the unit of the area RG comprising the map image MAP2 that is set on the measurement coordinate system CS of the perimetry through an operation of the input portion 19, watching a composite image PC2, as shown in FIG. 7. Receiving this, the main controller 11 instructs the concerned area setter 15 to set one or more areas RG designated by the operator as the concerned area NA, and to store these in a proper memory. In case of FIG. 7, fifteen areas RG are thus set on the upper side of X-axis of the measurement coordinate system CS as the concerned area NA, corresponding to the structural abnormality portion UP. The concerned area NA that was set is stored in the examination data memory 17 as the measurement data of the subject eye 22a together with the composite image PC2 and the other data, such as the examination date.

That is, the abnormality of the visual field is detected at the periphery of the structural abnormality portion UP in future with higher possibilities, and when setting the concerned area NA at such a periphery, it is possible to grasp the progress with higher sensitivity in future. In case of FIG. 7, the MD value in the whole visual field (weighting mean value of the total deviation with respect to all measurement points, that is, the measured values in all area RG (actually measured threshold values)) is +0.23 dB, that is plus value although the structural abnormality portion UP is found on the structure examination image PC1, and this value is higher than the mean threshold value SV. Then, normal range is judged in the mere perimetry results. On the other hand, the MD value regarding two or more areas RG comprising the concerned area NA (divided areas) is −0.89 dB, and is lower than the mean threshold value SV, and it is known that the area already shows the value lower than the normal threshold value SV. The stimulus operating portion 21 computes such a MD value as an evaluation value for the concerned area and the whole visual field through the instruction from the main controller 11 whenever the concerned area setter 15 sets the concerned area NA, and the result is outputted to the display 20 or an output device, such as a printer (not shown), and is stored in the examination data memory 17.

Because response stability is different in the center portion of the visual field and its peripheral portion, the weighting mean value is used for the total deviation. The response stability appears as a variability of the measured result, measurement sensitivity (threshold value) is good in the center of the visual field and less variability of the result appears. On the contrary, the measurement sensitivity (threshold value) is lower and the variability is bigger as approaching the periphery of the visual field. For this reason, the abnormality should be judged even if there are less depressions of the sensitivity in the center portion of the visual field. In case of the peripheral portion of the visual field, the resulting value may be within the variability range even if such a value is low to some extent. That is, even the same 1 dB change is different in the center portion and the peripheral portion of the visual field in the importance.

For this reason, Mean Deviation (MD value) that is generally used in the analysis of the perimetry result is computed as the mean value of the total deviation using a weighting factor (the difference between the normal value and the actually measured threshold value in each point). On such an occasion, "an inverse number of square value of the standard deviation" showing the variability in each measurement point (area RG) that is obtained from the database of the perimetry result of normal eyes is used as the weighting factor. An equation (1) is for obtaining the MD value with the weighting factor.

$$\left\{\frac{1}{n}\sum_{i=1}^{n}\frac{(X_i - Ni)}{S_{Ii}^2}\right\} \bigg/ \left\{\frac{1}{n}\sum_{i=1}^{n}\frac{1}{S_{Ii}^2}\right\} \qquad \text{Equation (1)}$$

wherein Xi is the actually measured threshold value in point i, Ni is the normal value in point i, and SIi is the standard deviation (dB) in point i. That is, the weighting factor is set every each measurement point, that is, every each area RG, and the MD value is obtained, adding the weighting factor.

The use of the weighting factor means quantity of the threshold value depression in each measurement point is equally evaluated. There are not many advantages even if the weighting factor is used in the narrow area, but it is possible to analyze, taking the importance of the visual field into consideration if the weighting factor is used when analyzing the wide area, such as the area including the center portion and its peripheral portion of the visual field, (the concerned area NA, for instance).

After thus storing the structure examination image PC1, the perimetry result, the composite image PC2, the concerned area NA and the MD value for the concerned area NA and the whole visual field for the subject eye 22a at some point of time in the examination data memory 17, the same examination is conducted for the subject eye 22a after every passage of predetermined time, such as every 6 months and every 1 year), and the structure examination image PC1, the perimetry result, the composite image PC2, the concerned area NA and the MD value for the concerned area NA and the whole visual field are stored every each such a time as the measurement data. Then, the change of the MD values regarding the concerned area NA and the whole visual field of the subject eye 22a is accumulated in the examination data memory 17.

Figure 8A:
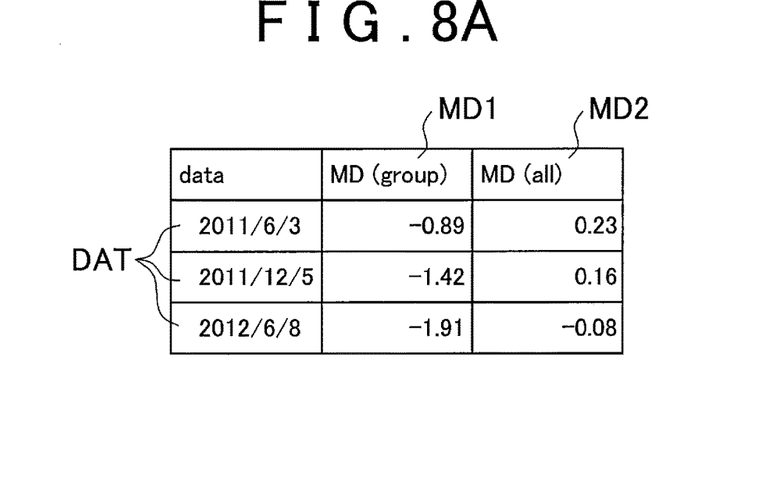
Figure 8B:
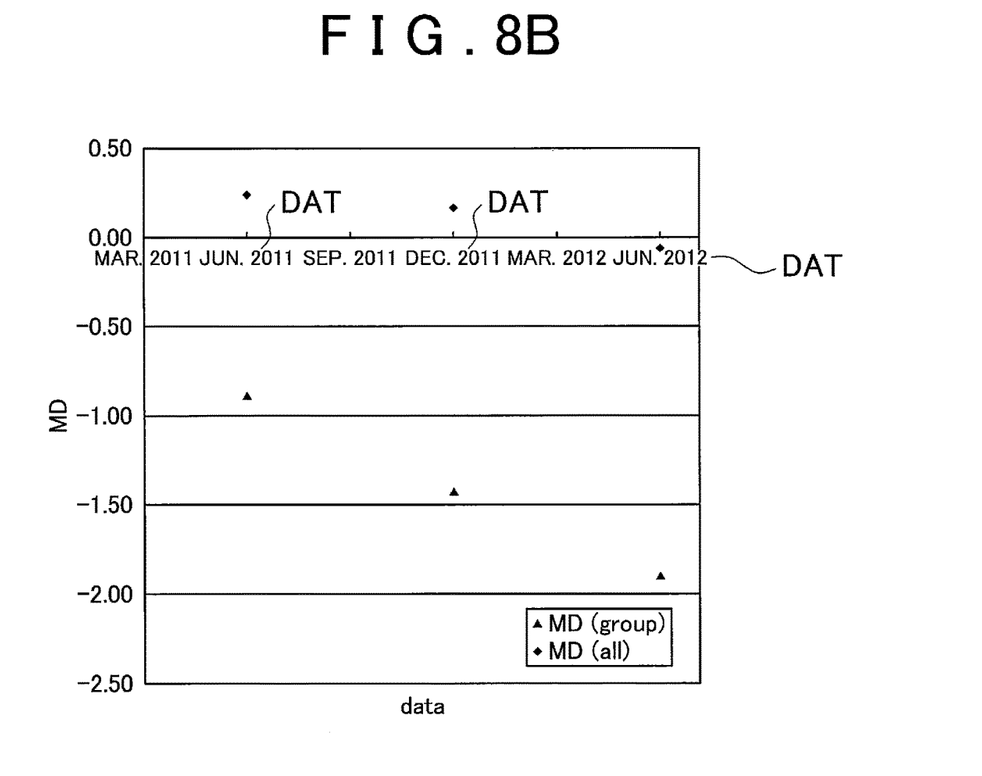

Then, the operator (the doctor) instructs through the input portion 19 at an optional point of time to indicate the change with time of the MD value for the concerned area NA and the whole visual field for the subject eye 22a of the examination data memory 17 as a figure of the visual field change, such as a table and a graph based upon the perimetry result at two or more past points of time in order to watch the change of condition of disease. Then, the main controller 11 instructs the result analysis portion 24 to indicate the MD value MD1 of the concerned area NA and the MD value MD2 of the whole visual field at this time every examination date DAT on the display 20 in the shape of a table based upon the data for the subject eye 22a that is stored in the examination data memory 17 as shown in FIG. 8(a), for instance, or to indicate these in the shape of a graph as shown in FIG. 8(b), and the result analysis portion 24 executes such an instruction. In a case where the perimetry data of the subject eye at many points of time is stored in the examination data memory 17, the table or the graph as shown in FIG. 8 may be composed and outputted based upon the perimetry data at two or more points of time that are selected by the operator through the input portion 19.

It is possible to designate one or more concerned areas NA since the structural abnormality portion UP itself may broaden in its area due to the progression of the disease or the abnormality may appear on the other portions. The operator designates one or more areas RG that are judged to conduct follow-up examination thereon over time, watching the composite image PC2, and the concerned area setter 15 sets one or more concerned areas NA. Since this concerned area NA can be set at an optional point of time, it is possible to newly set the concerned area NA from the examination result at some point of time and to search the change over time regarding the concerned area NA retroactively on the basis of the structure examination image PC1 and the perimetry result that are stored in the examination data memory 17. By doing so, it is possible to confirm from which point of time a dysfunction begins (or began). A good aspect of the invention is that it is possible to analyze the measurement result again retroactively.

The change of the concerned area NA every each examination does not necessarily lead to right evaluation. In a case where the concerned area NA is newly set broadens in the bounds in comparison with the previous concerned area NA or the sensitivity of the perimetry does not decrease so much in the area which newly broadened, there may be no difference between the MD values computed. For this reason, the attention is necessary. Then, preferably, the concerned area setter 15 records the setting change history of the concerned area NA, and if the operator changes the bounds of the concerned area NA, watching the structure examination image PC1, the stimulus operating portion 21 respectively computes and outputs the respective MD values regarding the concerned area NA before and after the change in order to give the operator an opportunity to let him (her) determine whether the setting of the concerned area NA is appropriate so that proper countermeasures can be taken to the inadvertent change of the concerned area NA.

A sector classification is known as a method to detect the abnormality and to confirm the change with time, paying an attention to only a part of the perimetry result as mentioned before. In such a sector classification method, the bounds of the visual field is divided into some groups (sectors) in advance, and the result is analyzed in each group, but, the concerned area NA is not optionally set based upon the structure examination image PC1 of the actual patient and the change of the concerned area NA with time is not monitored. When dividing into the sectors already determined, the abnormality portion of each person may not correspond to the sector, and for this reason there are many problems as to whether the structural change can be precisely detected. When the operator (the doctor) designates the area where the structural abnormality actually occurs on the structure examination image PC1 as the invention, the accurate follow-up is enable since there is not influence of the variability every patient.

In the invention, it is possible to confirm the change of the subject eye 22a with time by watching the portion showing the abnormality on the structure examination image PC1 and setting the concerned area NA. Besides, when setting the concerned area NA, it is possible to extract and evaluate only the portion showing the abnormality or only the portion showing the abnormality in future with higher possibility on the structure examination image PC1 and to improve judgment sensitivity regarding the progression of an illness.

Besides, it is possible to evaluate the progression of the illness, under the consideration of significance every measurement point, such as the area RG, by properly setting the concerned area NA comprising one or more areas RG as the invention. And, when superimposing the perimetry result on the structure examination image PC1 and comparing both, it is possible to easily confirm an occurrence of functional (visual field) abnormality with respect to the structure abnormality and the progression thereof and to easily take correspondence with the structural abnormality. As already mentioned, when superimposing the perimetry in the time when superimposing is not conducted on the structure examination image PC1, it is possible to newly evaluate the perimetry result and to effectively utilize the past perimetry without wasting. That is, it is not always necessary to superimpose the map image of the perimetry result on the structure examination image PC1 with the data in the same examination point of time.

EXPLANATION OF REFERENCE NUMBERS

2 . . . perimeter
10 . . . perimetry result indicator, threshold value measuring means (visual field measurer)
13 . . . structure examination image indicator (fundus image input portion)
15 . . . concerned area setter (concerned area setter)
16 . . . structural abnormality designator, composite image preparing means (composite image creator)
17 . . . memory (examination data memory)
19 . . . concerned area setter (input portion)
20 . . . display
21 . . . evaluation value computer (stimulus operating portion)
22a . . . subject eye
24 . . . perimetry result indicator, map image composer (result analysis portion)
NA . . . concerned area
RG . . . measurement point, divided area (area)
UP . . . structural abnormality portion
PC1 . . . structure examination image
MAP1, MAP2 . . . map image

The invention claimed is:

1. A perimeter for measuring a visual field of a subject eye by conducting predetermined perimetry operations for two or more measurement points of the subject eye, comprising: a memory that stores perimetry results; a perimetry result indicator that composes the perimetry result as a map image that corresponds to a fundus and indicates it on a display; a structure examination image indicator that obtains a structure examination image of the subject eye on which the perimetry is conducted and indicates the obtained image on the display; a composite image preparing means that superimposes the map image on the displayed structure examination image and indicates the superimposed on the display as a composite image; an input portion that is operated by an operator watching a composite image and designate concerned areas to be monitored regarding change-with-time by the unit of the area; a concerned area setter that sets a concerned area on the composite image by designating with the input portion; and an evaluation value computer that computes an evaluation value of the perimetry regarding the concerned area based upon the perimetry result and outputs it, wherein the memory stores the perimeter results of the subject eye in different times, and the evaluation value computer respectively computes and outputs the evaluation values of the perimetry at two or more points of time that are respectively different.

2. The perimeter according to claim 1 wherein the concerned area setter is able to set two or more concerned areas, and the evaluation value computer computes and outputs the evaluation values for the respective concerned areas.

3. The perimeter according to claim 1, wherein the memory stores a normal threshold value of each measurement point of the perimetry, and the perimeter further comprising:

a threshold value measuring means that measures a lowest value of brightness of a stimulus to which the subject eye can respond for two or more measurement points so as to obtain a threshold value examination result in each measurement point;
wherein the perimetry result indicator computes a deviation value regarding each measurement point from the measured threshold value examination result based upon the normal threshold value stored in the memory, and has a map image composer that composes the map image showing a total deviation result which is comprised of these deviation values.

4. The perimeter according to claim 1, further comprising a structural abnormality designator that sets a structural abnormality portion on the structure examination image indicated on the display, and indicate the set structural abnormality portion on the structure examination image.

* * * * *